US010052127B2

(12) United States Patent
Wood

(10) Patent No.: US 10,052,127 B2
(45) Date of Patent: Aug. 21, 2018

(54) CATHETERS FOR DEPLOYING IMPLANTABLE MEDICAL DEVICES, AND ASSOCIATED TETHERING ASSEMBLIES AND METHODS

(71) Applicant: Medtronic, Inc., Minneapolis, MN (US)

(72) Inventor: Rónán Wood, Co. na Gaillimhe (IE)

(73) Assignee: Medtronic, Inc., Minneapolis, MN (US)

( * ) Notice: Subject to any disclaimer, the term of this patent is extended or adjusted under 35 U.S.C. 154(b) by 527 days.

(21) Appl. No.: 14/630,832

(22) Filed: Feb. 25, 2015

(65) Prior Publication Data

US 2016/0243355 A1 Aug. 25, 2016

(51) Int. Cl.
*A61B 17/34* (2006.01)
*A61N 1/375* (2006.01)

(52) U.S. Cl.
CPC ........ *A61B 17/3468* (2013.01); *A61N 1/3756* (2013.01)

(58) Field of Classification Search
CPC .......... A61B 17/3468; A61B 2017/347; A61B 2017/22035; A61B 2017/00349; A61B 17/50; A61N 1/3756; A61N 1/362; A61N 1/37205; A61N 1/05; A61M 25/0029; A61M 25/0032; A61M 25/0071; A61M 25/007; A61M 2025/0036; A61M 2025/0037; A61M 2025/004; A61M 2025/0039

See application file for complete search history.

(56) References Cited

U.S. PATENT DOCUMENTS

| | | | | |
|---|---|---|---|---|
| 4,960,411 A | * | 10/1990 | Buchbinder | A61M 25/09033 600/434 |
| 5,344,402 A | * | 9/1994 | Crocker | A61M 25/1011 604/103.01 |
| 5,613,973 A | * | 3/1997 | Jackson | A61B 17/0218 606/1 |
| 6,190,353 B1 | * | 2/2001 | Makower | A61B 1/3137 600/137 |
| 7,011,671 B2 | | 3/2006 | Welch | |

(Continued)

OTHER PUBLICATIONS (PCT/US2016/018019) PCT Notification of Transmittal of the International Search Report and the Written Opinion of the International Searching Authority, dated May 2, 2016, 10 pages.

*Primary Examiner* — Jocelin Tanner

(57) ABSTRACT

An operator can release a looped portion of a tethering member, which terminates a distal section thereof, from being secured within a locking lumen of a delivery catheter shaft, and then move the distal section out of engagement with an attachment feature of an implantable medical device to untether the device from the catheter. The tethering member extends within another lumen of the shaft, which may be part of a catheter assembly that further includes a locking member extending within the locking lumen and having a distal tip located in proximity to an aperture of the shaft. To tether the device to the catheter, the operator can engage the tethering member distal section with the device attachment feature, and then pass the looped portion thereof through the aperture and into the locking lumen, where the locking member distal tip can be passed through the looped portion to secure it.

10 Claims, 10 Drawing Sheets

(56) References Cited

U.S. PATENT DOCUMENTS

| | | |
|---|---|---|
| 7,316,708 B2 | 1/2008 | Gordon et al. |
| 8,216,158 B2 | 7/2012 | Johnson |
| 8,615,310 B2 | 12/2013 | Khairkhahan et al. |
| 2005/0096666 A1* | 5/2005 | Gordon .............. A61B 17/3468 606/108 |
| 2007/0167974 A1* | 7/2007 | Cully .................. A61B 17/221 606/200 |
| 2012/0172891 A1 | 7/2012 | Lee |
| 2013/0103047 A1 | 4/2013 | Steingisser et al. |
| 2013/0253347 A1 | 9/2013 | Griswold et al. |

* cited by examiner

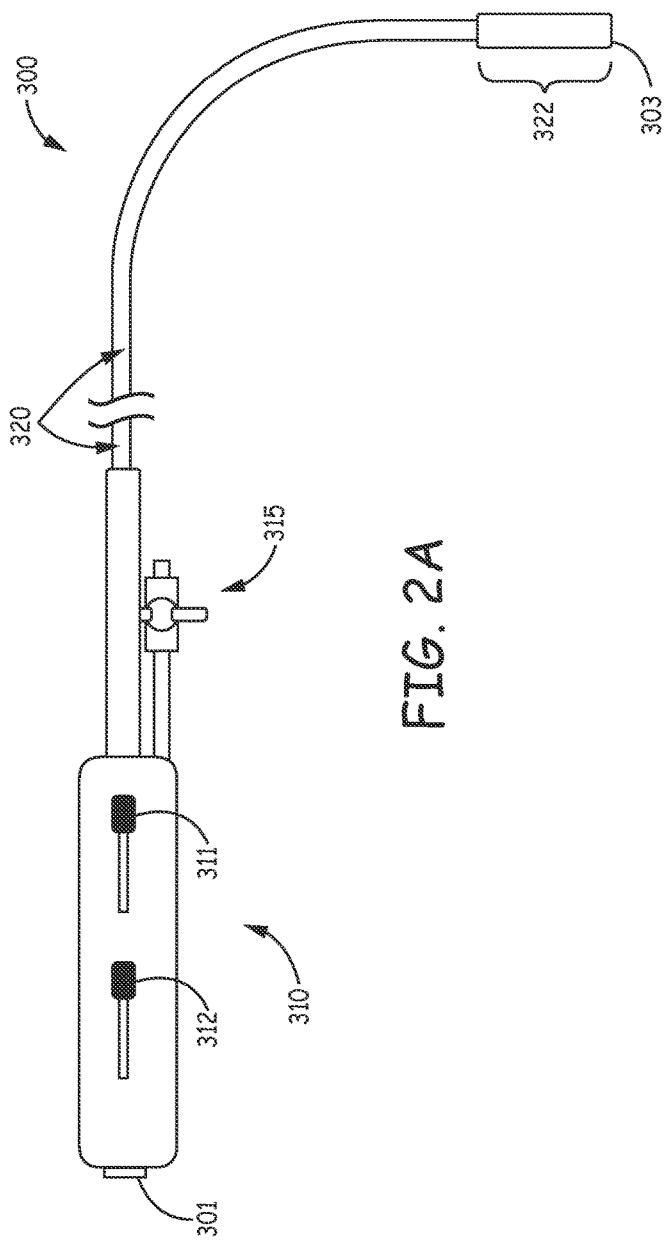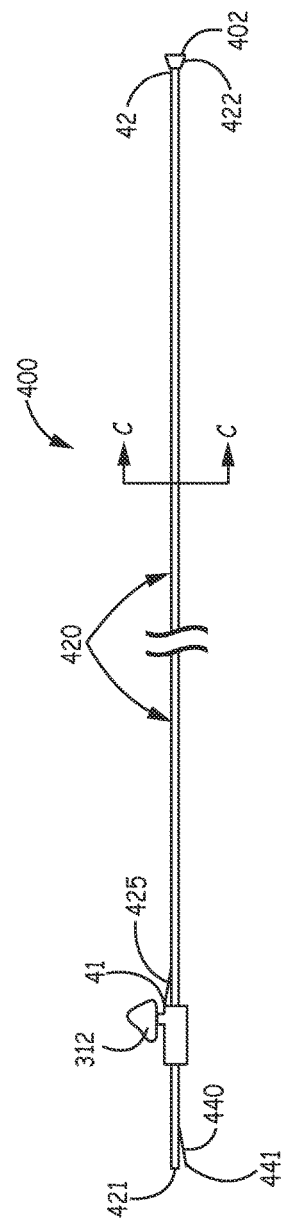

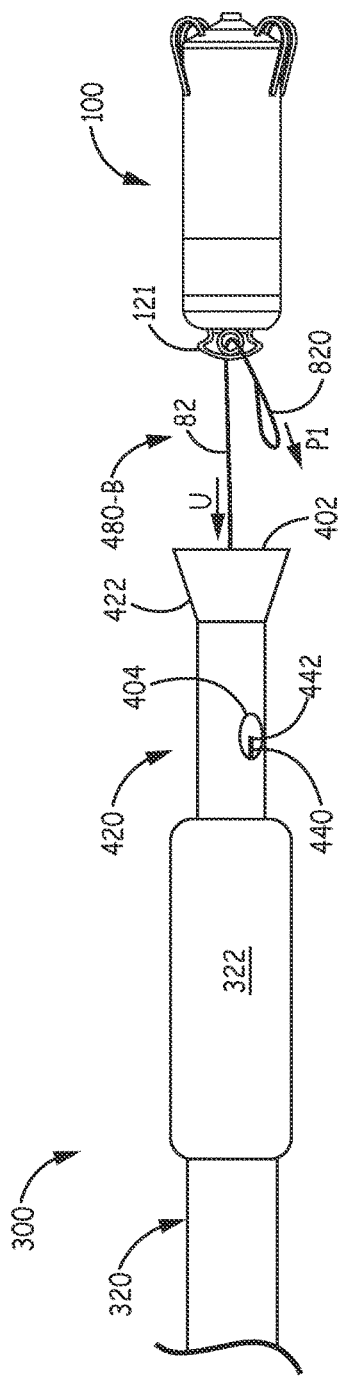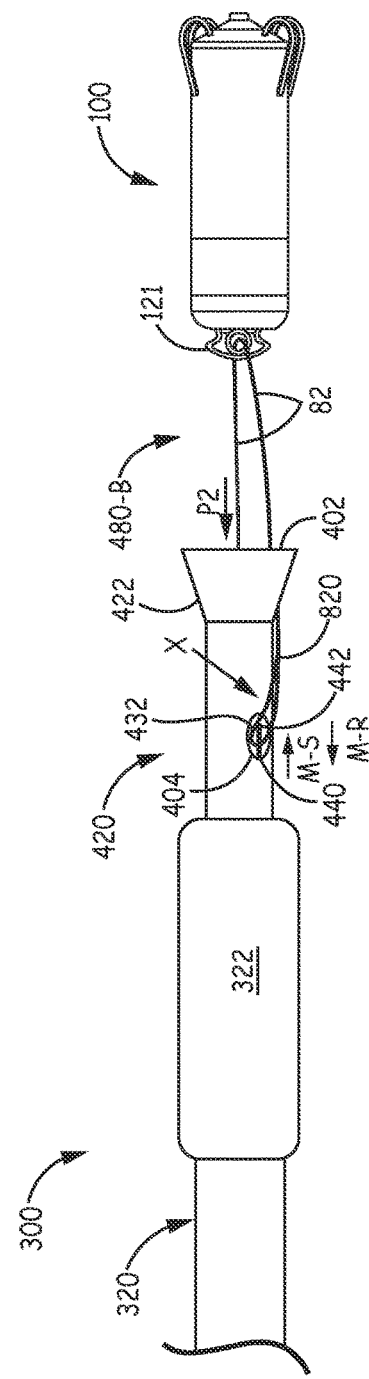
FIG. 5A
FIG. 5B

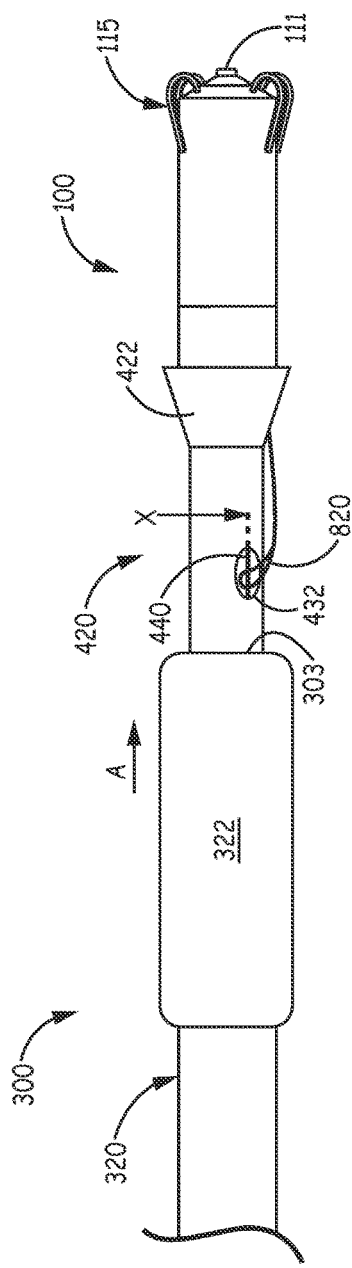
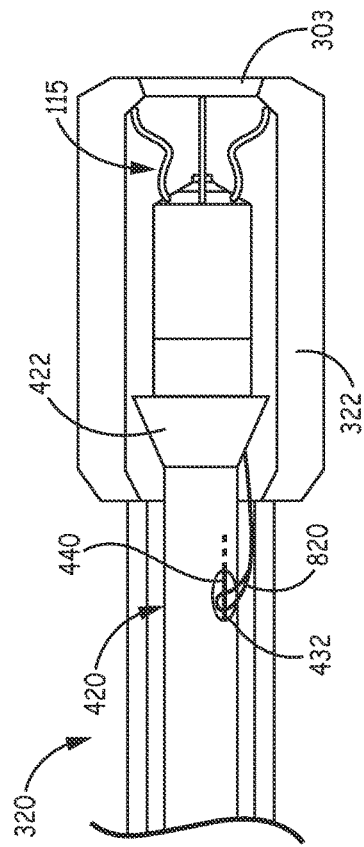
FIG. 5C
FIG. 5D

CATHETERS FOR DEPLOYING IMPLANTABLE MEDICAL DEVICES, AND ASSOCIATED TETHERING ASSEMBLIES AND METHODS

FIELD OF THE DISCLOSURE

The present disclosure pertains to catheters, and more particularly to catheters for deploying a relatively compact implantable medical device to an implant site, and associated tethering assemblies and methods.

BACKGROUND

The traditional implantable cardiac pacemaker includes a pulse generator device to which one or more flexible elongate lead wires are coupled. The device is typically implanted in a subcutaneous pocket, remote from the heart, and each of the one or more lead wires extends therefrom to a corresponding electrode, coupled thereto and positioned at a pacing site, either endocardial or epicardial. Mechanical complications and/or MRI compatibility issues, which are sometimes associated with elongate lead wires and well known to those skilled in the art, have motivated the development of implantable cardiac pacing devices that are wholly contained within a relatively compact package for implant in close proximity to the pacing site, for example, within the right ventricle RV of the heart. With reference to FIG. 1, such a device 100 is illustrated, wherein an hermetically sealed enclosure 105, preferably formed from a biocompatible and biostable metal such as titanium, contains a pulse generator, or an electronic controller and associated power source (not shown), to which at least one electrode 111 is coupled, for example, by a hermetic feedthrough assembly (not shown) like those known to those skilled in the. Enclosure 105 may be overlaid with an insulative layer, for example, medical grade polyurethane, parylene, or silicone, and a portion of the insulation layer may be removed to form another electrode 112, for example, to provide bipolar pacing and sensing in conjunction with electrode 111.

FIG. 1 shows device 100 having been deployed by an operator out from a distal opening 203 of a delivery catheter 200, which the operator has maneuvered up through the inferior vena cava IVC and the right atrium RA into the right ventricle RV. The deployed device 100 is shown fixed at an implant site by a fixation member 115 thereof, but still secured to catheter 200 by a tethering member 280 that extends out from distal opening 203 of catheter 200. Securing device 100 to catheter 200 with tethering member 280 is typically accomplished, prior to maneuvering catheter 200, with device 100 loaded therein, to the illustrated site, by looping tethering member 280 through an attachment feature 121 of device 100 and threading first and second lengths 281, 282 of tethering member 280 through one or more lumens of catheter 200 such that opposing ends thereof protrude out from a proximal opening 201 of catheter 200. After deploying device 100, the operator can grasp the ends of lengths 281, 282, for example, to tug on tethering member 280 to test the fixation of device 100 at the implant site, and/or to apply a greater force to tethering member 280 to remove device 100 from the implant site for repositioning at a more suitable site, if necessary. If satisfied with the implant of device 100, the operator can remove the looped tethering member 280 from engagement with device 100 by releasing, for example, the end of length 281, and then pulling on the end of the other length 282, thereby withdrawing an entirety of length 282 proximally through delivery catheter 200 so that the other length 281 is pulled distally and through device tether attachment feature 121, out from engagement therewith. Such a removal of tethering member 280 may tedious, particularly if blood has clotted around tethering member 280.

SUMMARY

Embodiments and methods of the present disclosure pertain to improved tethering of relatively compact implantable medical devices in the context of deploying the devices to an implant site via a delivery catheter, for example, to increase the ease of loading the devices into the delivery catheter and/or to increase the ease of untethering, or releasing the devices, after deployment, from securement to the delivery catheter.

According to some methods, after an operator initially deploys an implantable medical device at an implant site with a delivery catheter to which the device is secured by a distal section of an elongate tethering member, the operator can release a looped portion of the tethering member distal section, which terminates the distal section of the tethering member, from being secured within a locking lumen of a shaft of the catheter, and then pull a proximal section of the tethering member, which protrudes from a proximal end of the catheter, to move the distal section of the tethering member out of engagement with an attachment feature of the device.

According to some embodiments, the catheter for deploying the device includes an assembly of an elongate shaft, the elongate tethering member, and an elongate locking member, wherein the tethering member extends within a first lumen of the shaft and the locking member within a second (locking) lumen of the shaft. In these embodiments, the locking member includes a distal tip located in proximity to an aperture formed through a sidewall of the shaft, and the tethering member extends from a proximal section thereof to a distal section thereof within the first lumen, wherein the distal section, which is terminated by a looped portion thereof, protrudes from the first lumen at a distal end of the shaft, so that upon engaging the distal section with the attachment feature of the device, the operator can pass the looped portion through the aperture and into the second lumen, and then pass the distal tip of the locking member through the looped portion to secure the looped portion to the catheter shaft and thereby tether the device to the catheter. According to some embodiments, a handle assembly of the catheter includes a button coupled to a proximal end of the locking member for moving the distal tip of the locking member between a first location and a second location, the first location being distal to an entirety of the aperture (i.e., a securing location), and the second location being proximal to a distal edge of the aperture. According to some methods for loading the device into the delivery catheter, after securing the looped portion of the tethering member to the catheter shaft, as described above, the operator can pull the proximal section of the tethering member so that the engaged distal section of the tethering member brings the device into contact with the distal end of the catheter shaft.

BRIEF DESCRIPTION OF THE DRAWINGS

The following drawings are illustrative of particular embodiments of the present invention and therefore do not limit the scope of the invention. The drawings are not to scale (unless so stated) and are intended for use in conjunction with the explanations in the following detailed description. Embodiments will hereinafter be described in conjunction with the appended drawings wherein like numerals denote like elements, and:

FIG. 2A is a plan view of a delivery catheter, according to some embodiments;

FIG. 2B is a plan view of a shaft of the delivery catheter of FIG. 2A, according to some embodiments;

FIGS. 5A-D are schematics outlining some methods of the present invention; and

DETAILED DESCRIPTION

The following detailed description is exemplary in nature and is not intended to limit the scope, applicability, or configuration of the invention in any way. Rather, the following description provides practical examples, and those skilled in the art will recognize that some of the examples may have suitable alternatives.

Figure 1:
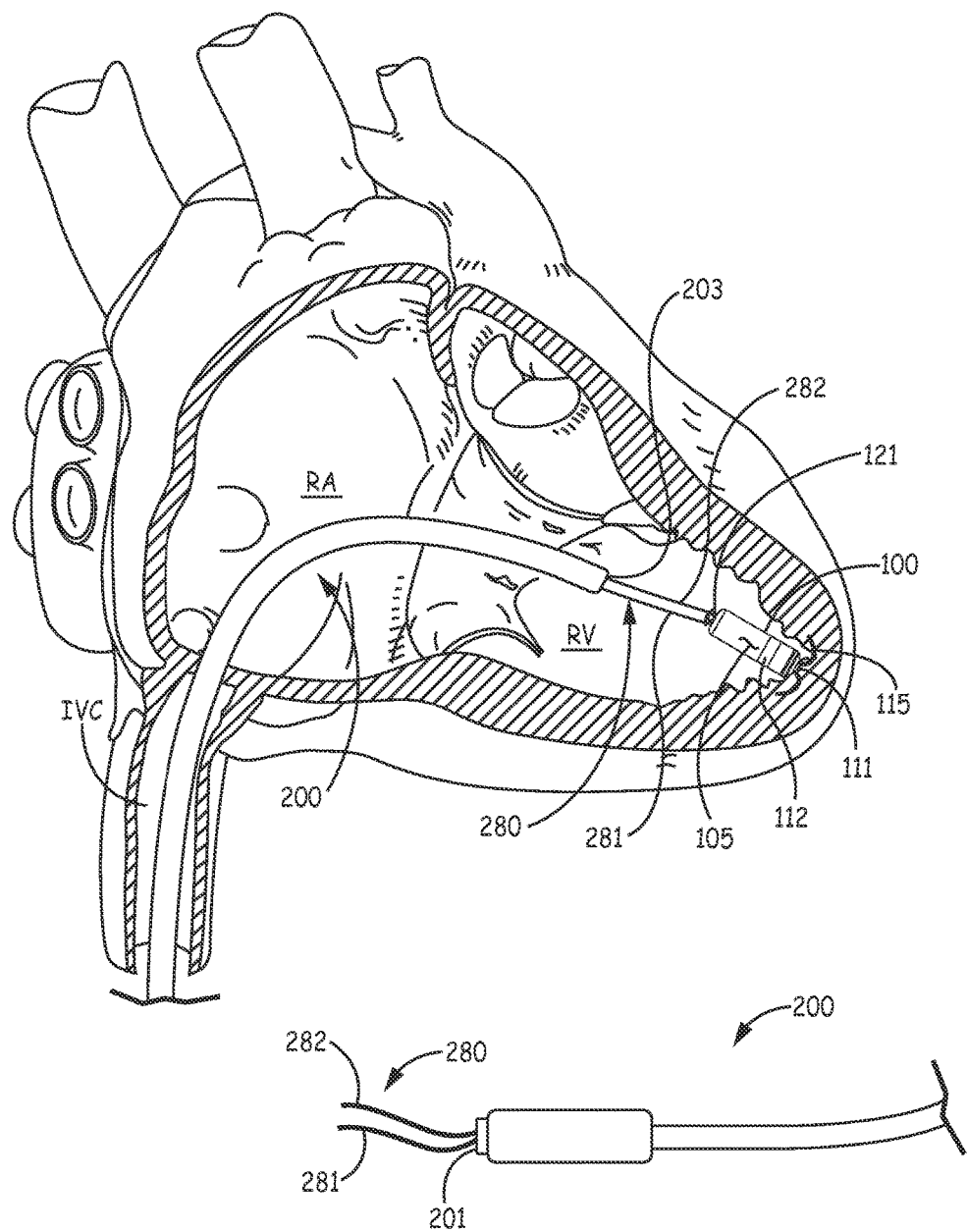
FIG. 1 is a schematic showing an exemplary implant of a relatively compact medical device, via an exemplary delivery catheter.

FIG. 2A is a plan view of a delivery catheter 300, according to some embodiments. FIG. 2A illustrates catheter 300 including a handle assembly 310, an outer tubular member 320, and a flushing assembly 315 coupled to handle assembly 310. FIG. 2A further illustrates a distal-most portion 322 of outer tubular member 320 defining a distal opening 303 thereof, and, as will be described in greater detail below, distal-most portion 322 is sized to contain an implantable medical device for deployment thereof. According to the illustrated embodiment, outer tubular member 320 is slideably engaged around a shaft 420, which is shown in the plan view of FIG. 2B, separate from a remainder of catheter 300, and outer tubular member 320 is coupled to a control member 311 of handle assembly 310, which is operable to retract and advance tubular member 320 relative to shaft 420. FIG. 2B illustrates shaft 420 extending from a proximal end 421 thereof to distal end 422 thereof, wherein distal end 422 forms a distal opening 402 of shaft 420 and is configured to engage with an implantable medical device (e.g. device 100 of FIG. 1). Delivery catheter 300 further includes an optional pull wire assembly, and FIG. 2B shows a proximal end 41 of a pull wire 425 extending out from shaft 420 to be coupled to a second control member 312 of handle assembly 310, wherein a distal end of pull wire 425 is anchored at a location 42, which is in proximity to distal end 422 of shaft 420. According to the illustrated embodiment, movement of second control member 312, actuates pull wire 425 to bend shaft 420 and outer tubular member 320, for example, to facilitate maneuvering delivery catheter 300 to an implant site.

Figure 2C:
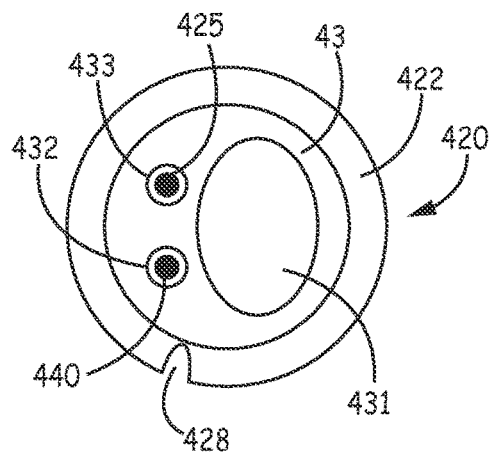
FIG. 2C is a cross-section view through section line C-C of FIG. 2B, according to some embodiments.

FIG. 2B further illustrates a proximal end 441 of an elongate locking member 440 extending from proximal end 421 of shaft 420. With reference to FIG. 2C, which is a cross-section view through section line C-C of FIG. 2B, pull wire 425 is shown extending within a lumen 433 of shaft 420, and locking member 440 is shown extending within another lumen 432 of shaft 420. According to some embodiments, shaft 420 is formed, at least in part, by a multi-lumen tube 43, which may be extruded polyether block amide, polyurethane, or silicone rubber, or a composite thereof, and may include an overlay (not shown), for example, formed of braid-reinforced polyether block amide. With further reference to FIG. 2C, multi-lumen tube 43 includes the two, relatively small lumens 432, 433, and one, relatively large lumen 431, wherein lumen 341 is in fluid communication with distal opening 402 of shaft 320 and with a proximal port 301 of handle assembly 310 (FIG. 2A). With reference to FIG. 4B, which will be described in greater detail below, proximal end 421 of shaft 420 is shown secured within handle assembly 310 so that lumen 431 is also in fluid communication with flushing assembly 315. According to the illustrated embodiment, lumen 431 provides a passageway through which a tethering member, for example, either of the embodiments shown in FIGS. 3A-B, can extend to secure an implantable medical device, such as device 100, to catheter 300, as described in greater detail below.

Figure 2D:
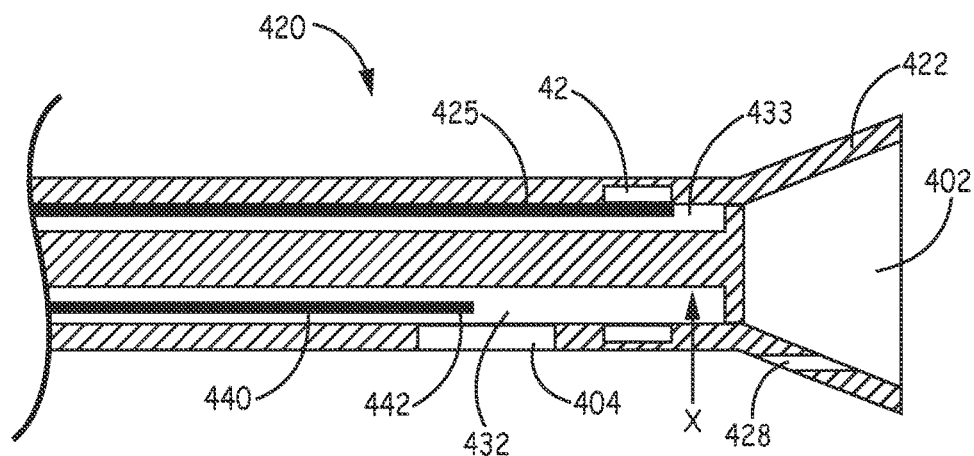
FIG. 2D is an enlarged longitudinal cross-section view of a distal portion of the catheter shaft shown in FIG. 2B, according to some embodiments.

FIG. 2D is an enlarged longitudinal cross-section view of a distal portion of catheter shaft 420, according to some embodiments, wherein a distal tip 442 of locking member 440 can be seen. With reference back to FIGS. 2B-C, locking member extends from proximal end 441 thereof to distal tip 442 thereof within lumen 432 of shaft 440. FIG. 2D illustrates shaft 440 including an aperture 404 formed through a sidewall thereof in proximity to distal end 422, wherein aperture 404 provides access to lumen 432 and to distal tip 442 of locking member 440 therein. Distal tip 442 is shown located proximal to a distal edge of aperture 404, but is moveable within lumen 432 between the illustrated location and another location X, which is distal to an entirety of aperture 404. According to some preferred embodiments, lumen 432 is terminated at an end wall in proximity to location X, as shown; alternately, lumen 432 extends to, or through distal end 422. Locking member 440 may be formed from a relatively rigid metal wire, for example, having a diameter of approximately 0.010 inch. The function of locking member 440 within catheter 300 is described below in conjunction with FIGS. 5A-C.

Figure 3A:
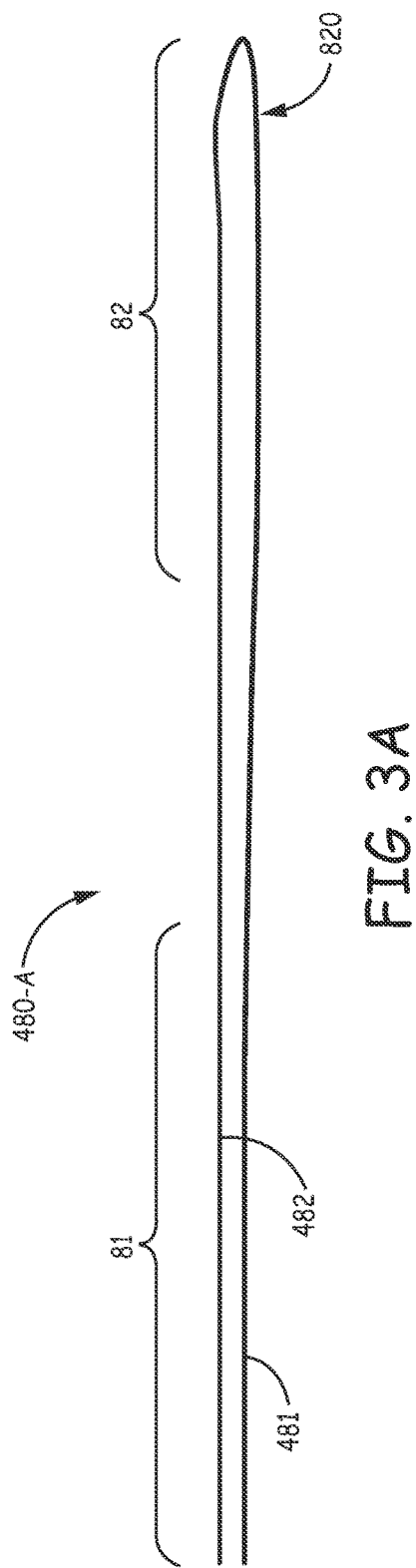
FIGS. 3A-B are plan views of alternate embodiments of a tethering member that may be employed in the catheter of FIGS. 2A-D.
Figure 3B:
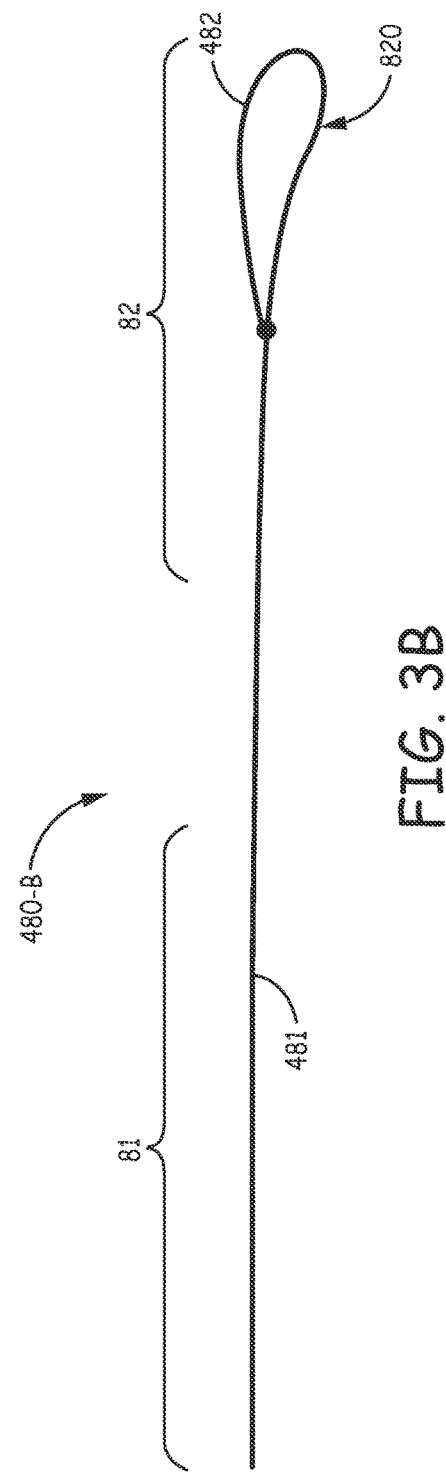

FIGS. 3A-B are plan views of alternative tethering members 480-A, 480-B, which may be employed by delivery catheter 300. FIG. 3A illustrates tethering member 480-A including first and second lengths 481, 482 folded alongside one another so that a distal section 82 of tethering member 480-A includes a looped portion 820 where first and second lengths 481, 482 meet, and a proximal section 81 of tethering member 480-A includes terminal ends of each length 481, 482. FIG. 3B illustrates tethering member 480-B also including first and second lengths 481, 482, and proximal and distal sections 81, 82, but the terminal end of second length 482 is joined to first length 481 along distal section 82 to form looped portion 820. Each tethering member 480-A, 480-B may be formed from a polyester fiber having a fluoropolymer coating, such as PTFE. As indicated above, either of tethering members 480-A, 480-B may extend from the corresponding proximal section 81 to the corresponding distal section 82 within lumen 431 of catheter shaft 420 (FIG. 2C), and FIG. 4A is a plan view of delivery catheter 300 in which tethering member 480-B is employed as such.

Figure 4A:
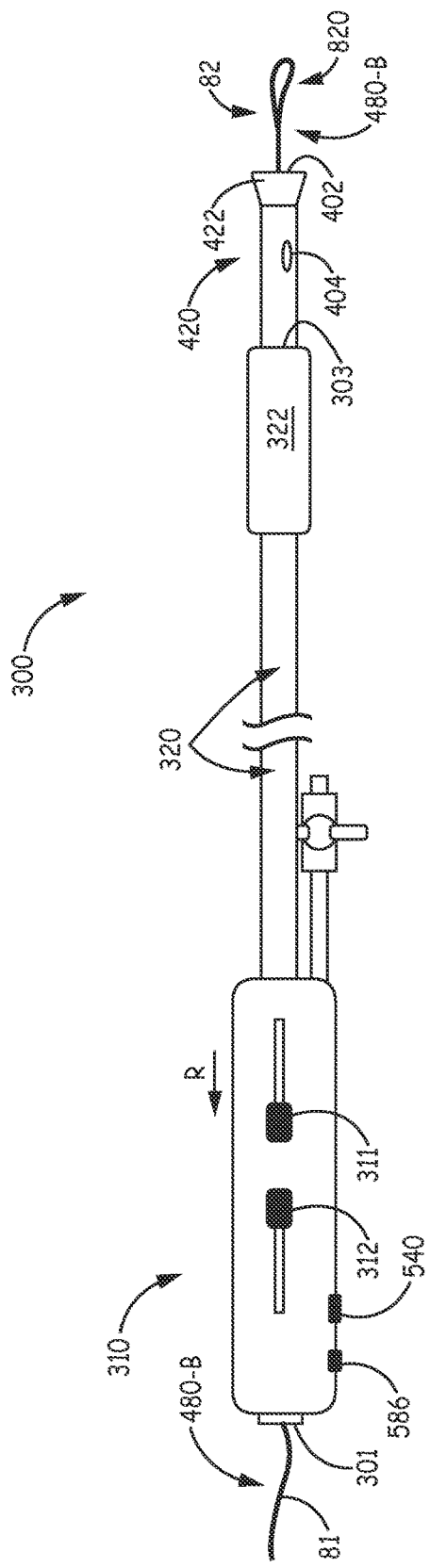
FIG. 4A is a plan view the delivery catheter, according to some embodiments.
Figure 4B:
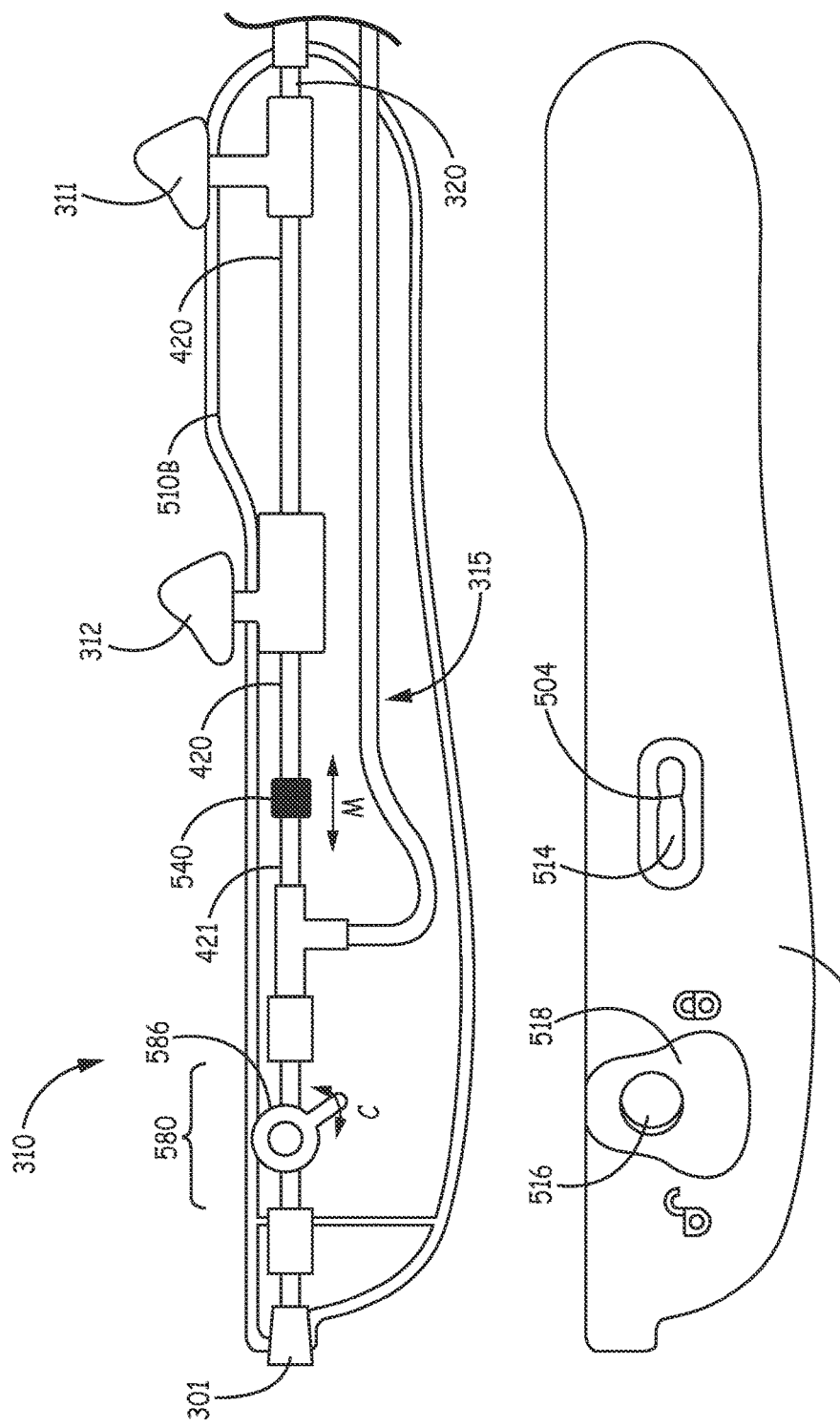
FIG. 4B is an interior plan view of a handle assembly of the delivery catheter, according to some embodiments.

FIG. 4A illustrates proximal section 481 of tethering member 480-B protruding out from proximal port 301 of handle assembly 310, and distal section 82 of tethering member 480-B protruding out from distal opening 402 of catheter shaft 420. According to the illustrated embodiment, proximal section 81 of tethering member 480-B can be clamped within handle assembly 310 via actuation of a knob 586 of a valve member 580 that is integrated into a conduit of handle assembly 310, for example, as shown in FIG. 4B.

FIG. 4B is a plan view of an internal configuration of handle assembly 310 wherein a first portion of an outer surface, or shell 510A of handle assembly 310 is removed to see an arrangement of components within a second portion of the shell 510B. According to an exemplary embodiment, valve member 580 is constructed like a stop-cock valve known to those skilled in the art, and first portion of shell 510A includes an aperture 516 formed through a recessed surface 518 thereof, which provides access to knob 586 of valve member 580, so that an operator can rotate knob 586 between an open position and a closed position, per arrow C. The open position allows free movement of tethering member 480-B within shaft 420, while the closed position clamps down on proximal section 81 of tethering member 480-B. FIG. 4B illustrates a button 540 located in proximity to proximal end 421 of catheter shaft 420 and a corresponding aperture 514 formed through first portion of shell 510A to provide the operator access to button 540. With reference back to FIG. 2B, according to some embodiments, button 540 is coupled to proximal end 441 of locking member 440, so that the operator can move distal tip 442 of locking member 440 between the above-described locations, relative to aperture 404 (FIG. 2D), by moving button 540 proximally and distally, per arrow M. FIG. 4B further illustrates an optional detent feature 504 formed along an edge of aperture 514 to engage a neck of button 540 and thereby provide some resistance to accidentally moving button 540 proximally from a distal location that positions locking member distal tip 442 distal to an entirety of aperture 404, for example, at location X. Alternately a safety catch or toggle member may be integrated into handle assembly 310 to prevent accidental movement of button 540 from the distal location.

With further reference to FIG. 4A, outer tubular member 320 is shown having been retracted relative to shaft 420, for example, by moving control member 311 proximally, per arrow R, so that aperture 404 of shaft 420 is exposed distal to distal-most portion 322 of outer tubular member 320. With delivery catheter 300 in this illustrated configuration, a relatively compact implantable medical device (e.g., device 100) can be loaded therein, for example, according to methods outlined in conjunction with FIGS. 5A-D.

FIG. 5A shows distal section 82 of tethering member 480-B having been engaged with attachment feature 121 of device 100, for example, by threading distal section 82 through an opening thereof. FIG. 5A further illustrates looped portion 820 of the engaged distal section 82 being pulled proximally, per arrow P1, toward aperture 404 of catheter shaft 420, while distal tip 442 of locking member 440, within lumen 432, is located proximal to the distal edge of aperture 404. In FIG. 5B, the operator has passed looped portion 820 of tethering member 480-B through aperture 404 and into lumen 432 so that distal tip 442 of locking member 440 can be passed through looped portion 820 and moved, per arrow M-S, into location X, distal to an entirety to aperture 404, for example, as shown with a dashed line in FIG. 5C.

With further reference to FIG. 5B, after moving distal tip 442, per arrow M-S, the operator can pull proximal section 81 of tethering member 480-B (FIG. 4A) to bring device 100 into contact with distal end 422 of catheter shaft 440, per arrow P2, and then, according to some methods, rotate knob 586 of valve member 580 (FIG. 4B) to clamp down on proximal section 81 in handle assembly 310, and thereby secure proximal section 81 to the proximal end of catheter 300. With further reference to FIG. 5C, after bringing device 100 into contact with distal end 422 of catheter shaft 420, the operator can advance outer tubular member 320, per arrow A, over shaft distal end 422 and device 100, for example, as shown in FIG. 5D.

The figures illustrate distal end 422 of catheter shaft 420 being enlarged from a remainder of shaft 420 to enclose attachment feature 121 and generally conform to a proximal end of device 100, according to some embodiments. In these embodiments, distal end 422 may include a passageway 428 formed therein, for example, a groove, as seen in the cross-section view of FIG. 2C, or a hole as seen in FIG. 2D. Passageway 428 can receive insertion of distal section 82 of tethering member 480-B therethrough, after the operator engages distal section 82 with attachment feature 121, for example, when the operator passes looped portion 820 through aperture 404 and into lumen 432 of shaft 440. According to some alternate embodiments, distal end 422 of shaft 420 need not be enlarged and need not include passageway 428.

With further reference to FIG. 5D, an interior of distal-most portion 322 of outer tubular member 320 is shown being sized to contain device 100 and shaft distal end 422 in contact therewith. According to the illustrated embodiment, advancing outer tubular member 320 over device 100 moves a plurality of fixation fingers of fixation member 115 from a relaxed condition (FIGS. 5A-C) to an extended condition shown in FIG. 5D. Fixation member 115 may be cut from Nitinol tubing, according to methods known in the art, and the super-elastic nature of Nitinol allows the fingers thereof to elastically deform between the relaxed and extended conditions. The extended condition of the fixation fingers allows for initial engagement thereof with tissue, when catheter 300 is employed to deploy device 100 at an implant site, for example, according to some methods described in conjunction with the schematics of FIG. 1 and FIGS. 6A-C.

Figure 6A:
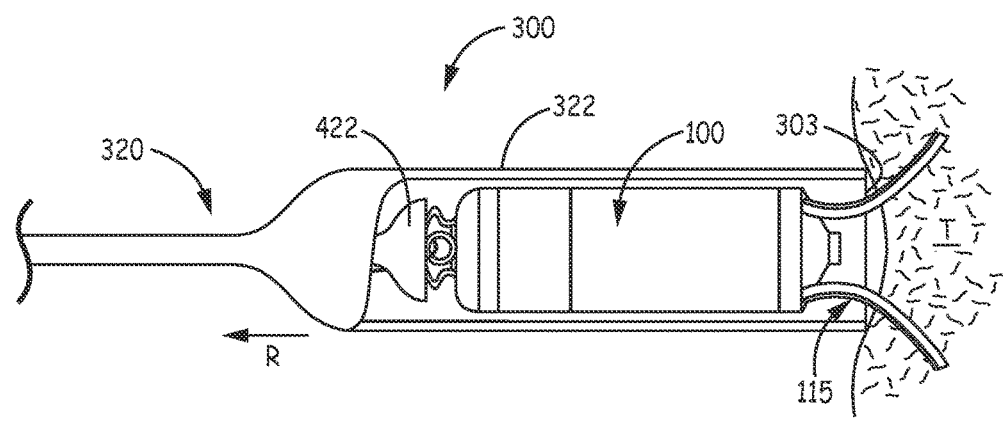
FIGS. 6A-C are schematics outlining some additional methods.
Figure 6B:
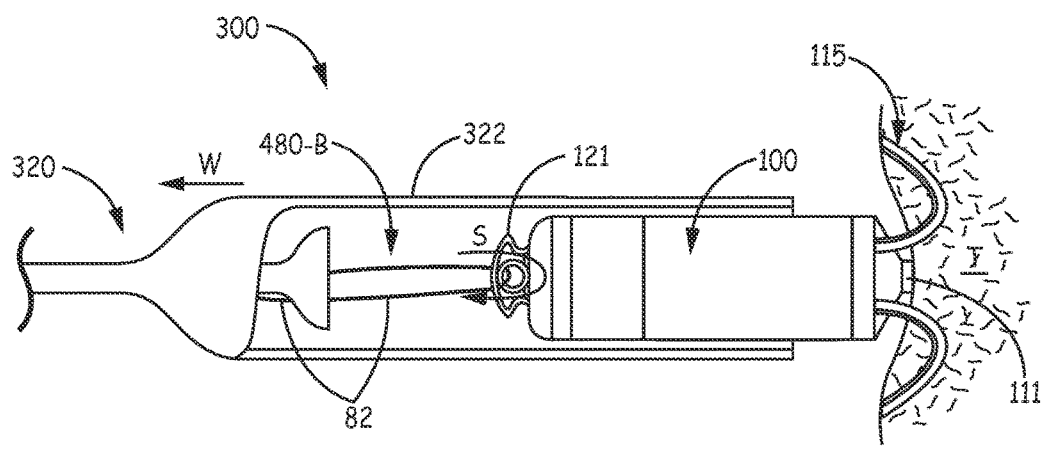

Catheter 300, after device 100 is loaded therein, may be advanced by the operator into a body of a patient and maneuvered into proximity with an implant site. With reference back to FIG. 1, catheter 300, like catheter 200, can be maneuvered up through the inferior vena cava IVC and into the right ventricle RV, from the right atrium RA, to approach an implant site. FIG. 6A shows fingers of device fixation member 150 initially engaging tissue T at the implant site as outer tubular member 320 of catheter is retracted, per arrow R. When fixation member 150 of device 100 is fully engaged with tissue T, as seen in FIG. 6B, delivery catheter 300 can be withdrawn, per arrow W. If the operator previously clamped down on proximal section 81 of tethering member 480-B, when loading device 100 into catheter 300, by rotating knob 586 to close valve member 580 of handle assembly 310 (FIG. 4B), the operator now rotates knob 586 in an opposite direction to open valve member 580, thereby allowing free movement of tethering member 480-B within shaft 420 while withdrawing catheter 300. According to some methods, after opening valve member 580, the operator may tug on proximal section 81 of tethering member 480-B to test the fixation of device 100 at the implant site, and then, if fixation is adequate, proceed to withdraw catheter 300 away from device 100.

Figure 6C:
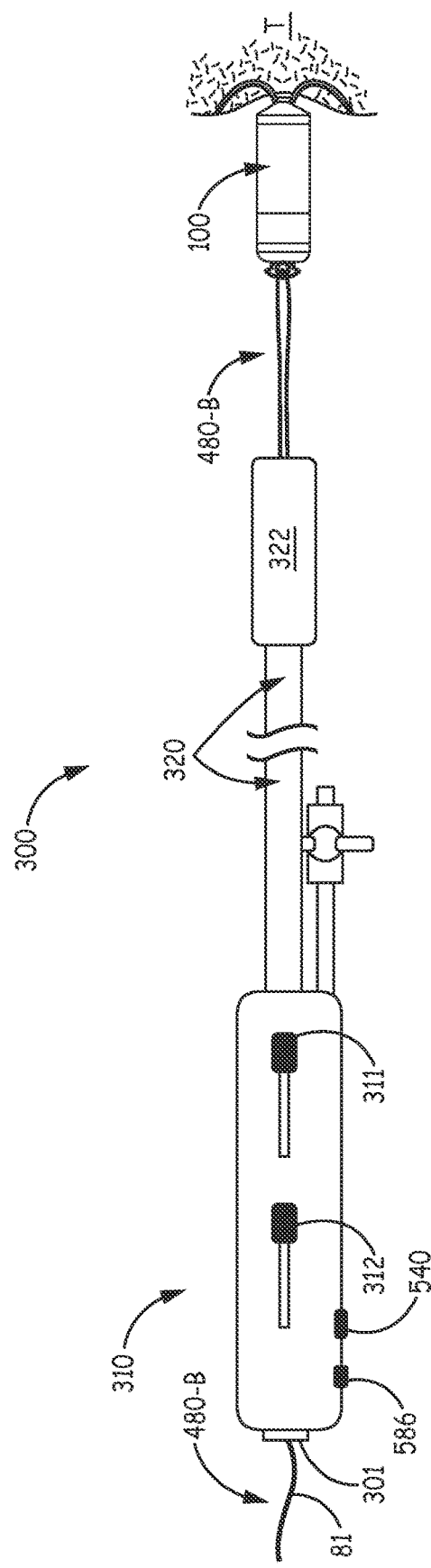

With further reference to FIG. 6B, because distal section 82 of tethering member 480-B is still secured to catheter 300 (by locking member 440 in lumen 432), the withdrawal of catheter 300 pulls tethering member 480-B through the opening of device attachment feature 121, per arrow S. But, with reference to FIG. 6C, a length of proximal section 81 of tethering member 480-B is long enough to still protrude from proximal port 301 of catheter 300, so that the operator can maintain control over the tethering of device 100 to catheter 300, until the operator determines that device 100 can be untethered from catheter 300. FIG. 6C shows device 100 fixed to tissue T at the implant site and still tethered, but with catheter 300 withdrawn a distance from device 100 so that the operator can evaluate the performance of device 100, for example, pacing and sensing, without mechanical interference from catheter 300. If the operator finds the performance of device 100 satisfactory, device 100 can be untethered and catheter 300 completely withdrawn from the body of the patient. According to some methods for untethering device 100, the operator releases looped portion 820 of distal section 82 of tethering member 480-B from being secured in lumen 432 (FIG. 5C), by moving distal tip 442 of locking member 440 per arrow M-R of FIG. 5B, which may be accomplished via button 540 (FIG. 4B), and then by pulling proximal section 81 of tethering member 480-B to disengage distal section 82 from attachment feature 121 of device 100, per arrow U of FIG. 5A.

In the foregoing detailed description, the invention has been described with reference to specific embodiments. However, it may be appreciated that various modifications and changes can be made without departing from the scope of the invention as set forth in the appended claims.

The invention claimed is:

1. A delivery catheter for deploying a relatively compact implantable medical device to an implant site, the catheter comprising:
   an elongate shaft extending from a proximal end thereof to a distal end thereof, the shaft including a first lumen, a second lumen, and an aperture formed through a sidewall of the shaft and being located in proximity to, and proximal to the distal end of the shaft, the aperture providing access to the second lumen through the sidewall;
   an elongate tethering member extending from a proximal section thereof to a distal section thereof within the first lumen of the shaft, the distal section protruding from the first lumen at the distal end of the shaft, being configured for engaging with an attachment feature of the implantable medical device, and including a looped portion that terminates the distal section, and the aperture of the shaft being sized to allow passage of the looped portion therethrough and into the second lumen of the shaft; and
   an elongate locking member extending from a proximal end thereof to a distal tip thereof within the second lumen of the shaft, the distal tip being located in proximity to the aperture of the shaft, and the distal tip being configured to pass through the looped portion of the distal section of the tethering member; and
   a handle assembly coupled to the proximal end of the shaft, the proximal section of the tethering member protruding from the handle assembly, the handle assembly including a button coupled to the proximal end of the locking member for moving the distal tip of the locking member between a first location and a second location, the first location being distal to and entirety of the aperture, and the second location being proximal to a distal edge of the aperture.

2. The catheter of claim 1, wherein the distal end of the shaft is enlarged from a remainder of the shaft, being configured to generally conform to a proximal end of the implantable medical device.

3. The catheter of claim 2, the distal end of the shaft includes a passageway formed therein, the passageway configured to receive the distal section of the tethering member, when the looped portion thereof is passed through the aperture and into the second lumen of the shaft.

4. The catheter of claim 1, further comprising:
   a pull wire assembly including an elongate pull wire and an anchor band, the pull wire extending from a proximal end thereof to a distal end thereof, and the anchor band being mounted to the shaft and coupled to the distal end of the pull wire; and
   wherein the shaft further includes a third lumen in which the pull wire extends; and
   the handle assembly further includes a control member coupled to the proximal end of the pull wire.

5. The catheter of claim 1, wherein the handle assembly further includes a clamping subassembly, the clamping subassembly being operable to secure the proximal section of the tethering member within the handle assembly.

6. The catheter of claim 1, further comprising an elongate outer tubular member slideably engaged around the shaft, the outer tubular member including a distal-most portion sized to contain the medical device and the distal end of the shaft therein, when the medical device is in contact with the distal end of the shaft.

7. An assembly for a delivery catheter, the catheter for deploying a relatively compact implantable medical device to an implant site, and the assembly comprising:
   an elongate shaft extending from a proximal end thereof to a distal end thereof, the shaft including a first lumen, a second lumen, and an aperture formed through a sidewall of the shaft and being located in proximity to, and proximal to the distal end of the shaft, the aperture providing access to the second lumen through the sidewall;
   an elongate tethering member extending from a proximal section thereof to a distal section thereof within the first lumen of the shaft, the proximal section protruding from the first lumen at the proximal end of the shaft, the distal section protruding from the first lumen at the distal end of the shaft, being configured for engaging with an attachment feature of the implantable medical device, and including a looped portion that terminates the distal section, and the aperture of the shaft being sized to allow passage of the looped portion therethrough and into the second lumen of the shaft; and
   an elongate locking member extending from a proximal end thereof to a distal tip thereof within the second lumen of the shaft, the distal tip being configured to pass through the looped portion of the distal section of the tethering member, and the distal tip being moveable with the second lumen between a first location and a second location, the first location being distal to an entirety of the aperture, and the second location being proximal to a distal edge of the aperture.

8. The assembly of claim 7, wherein the distal end of the shaft is enlarged from a remainder of the shaft, being configured to generally conform to a proximal end of the implantable medical device.

9. The assembly of claim 8, the distal end of the shaft includes a passageway formed therein, the passageway configured to receive the distal section of the tethering member, when the looped portion thereof is passed through the aperture and into the second lumen of the shaft.

10. The assembly of claim 7, wherein the shaft further includes a third lumen and a pull wire sub-assembly, the pull wire sub-assembly including an elongate pull wire, and an anchor band, the pull wire extending within the third lumen, from a proximal end thereof to a distal end thereof, and the pull band being mounted to the shaft and coupled to the distal end of the pull wire.

\* \* \* \* \*